United States Patent
Li et al.

(10) Patent No.: US 8,922,219 B2
(45) Date of Patent: Dec. 30, 2014

(54) PHOTO-IONIZATION DETECTORS AND ASSOCIATED METHODS THEREOF

(75) Inventors: Bo Li, Rexford, NY (US); Rui Chen, Clifton Park, NY (US); Matthew Damian Pietrzykowski, Clifton Park, NY (US); Xuefeng Wang, Schenectady, NY (US); Nannan Chen, Clifton Park, NY (US); Cheng-Po Chen, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 492 days.

(21) Appl. No.: 12/956,953

(22) Filed: Nov. 30, 2010

(65) Prior Publication Data

US 2012/0136268 A1    May 31, 2012

(51) Int. Cl.
   *G01N 27/62* (2006.01)
   *G01N 27/66* (2006.01)
   *G01N 27/70* (2006.01)
   *G01N 33/497* (2006.01)

(52) U.S. Cl.
   CPC .............. *G01N 27/66* (2013.01); *G01N 27/70* (2013.01); *G01N 33/497* (2013.01)
   USPC ......................................... 324/464; 324/459

(58) Field of Classification Search
   CPC ....... G01N 27/66; G01N 30/62; G01N 30/64; G01N 21/783; G01N 27/62; G01N 27/64; G01N 27/70; A61B 5/083
   USPC .................................. 324/464, 459
   See application file for complete search history.

(56) References Cited

U.S. PATENT DOCUMENTS

| | | | |
|---|---|---|---|
| 4,377,749 | A | 3/1983 | Young |
| 4,398,152 | A | 8/1983 | Leveson |
| 4,804,846 | A | 2/1989 | Hall |
| 4,866,278 | A | 9/1989 | Lovelock |
| 5,773,833 | A | 6/1998 | Hsi |
| 6,225,633 | B1 | 5/2001 | Sun et al. |
| 6,313,638 | B1 | 11/2001 | Sun et al. |
| 7,046,012 | B2 | 5/2006 | Dean et al. |
| 7,530,257 | B2 | 5/2009 | Bonne |
| 2007/0173731 | A1* | 7/2007 | Meka et al. ................... 600/543 |
| 2008/0176317 | A1* | 7/2008 | Kirollos et al. ............ 435/288.7 |
| 2008/0314115 | A1* | 12/2008 | Faulder et al. ................. 73/23.3 |

FOREIGN PATENT DOCUMENTS

| | | |
|---|---|---|
| EP | 0573060 B1 | 2/2000 |
| EP | 0995989 A1 | 4/2000 |
| EP | 1331477 A2 | 7/2003 |
| EP | 2148194 A1 | 1/2010 |

OTHER PUBLICATIONS

EP11189472 Search Report and Written Opinion, Apr. 18, 2012.
Z. Xie et al., "Determination of acetone, 2-butanone, diethyl ketone and BTX using HSCC-UV-IMS", Anal Bioanal Chem, vol. 372, Mar. 2002, pp. 606-610.

* cited by examiner

*Primary Examiner* — Amy He
(74) *Attorney, Agent, or Firm* — Melissa K. Dobson

(57) ABSTRACT

A photo ionization detector (PID) is provided for selectively determining various compounds or gases present in a breath sample. The PID, comprises a substrate comprising a gas ionization chamber, at least one pair of ion sensing electrodes, and at least one amplifying circuit; and an ultraviolet (UV) ionization source to transmit a UV light beam into the gas ionization chamber. A system comprises the PID is also provided. A method of detecting a response pattern for various compounds or gases in breath using PID is also provided.

7 Claims, 17 Drawing Sheets

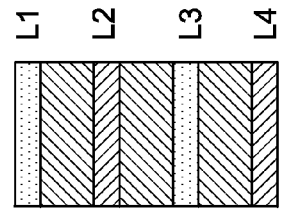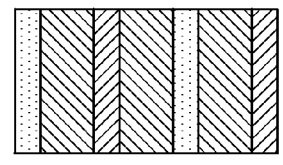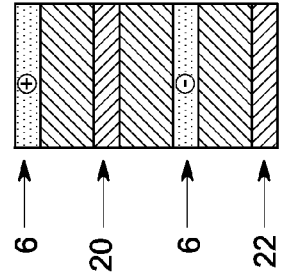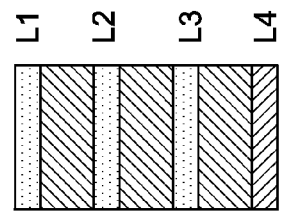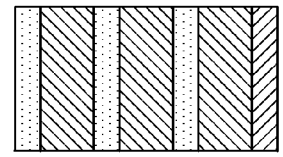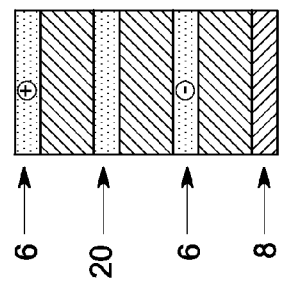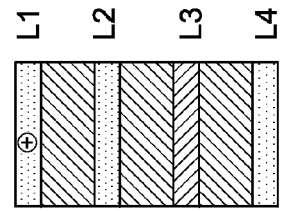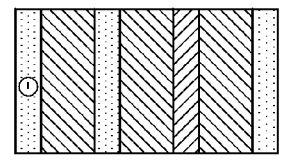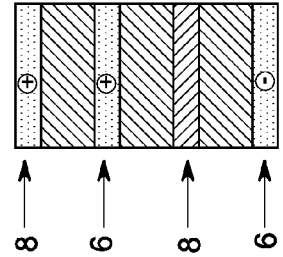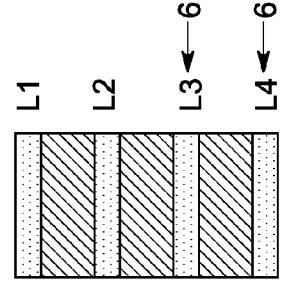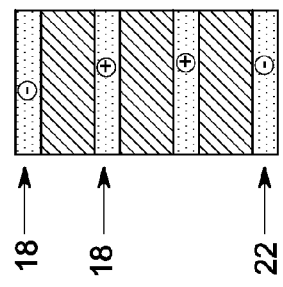

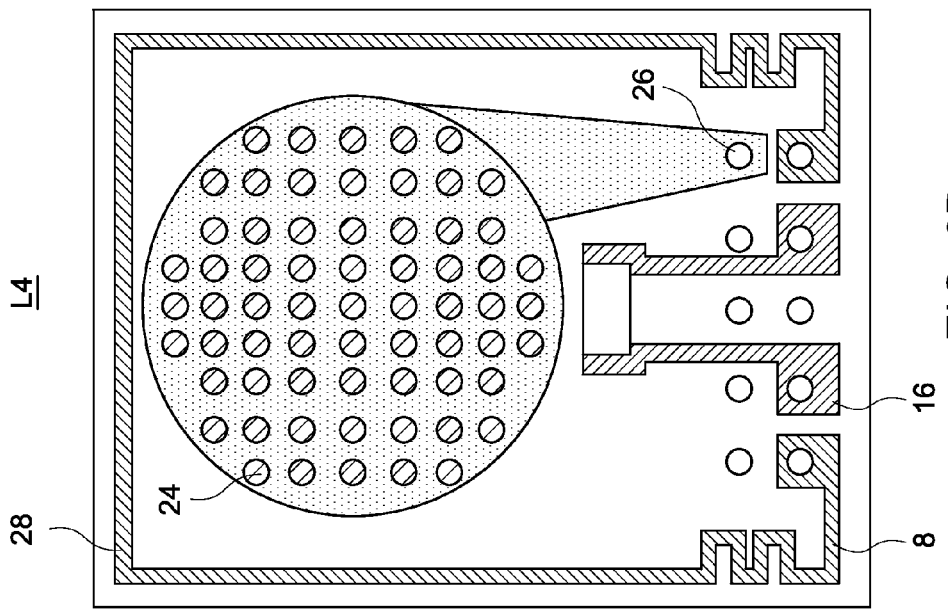
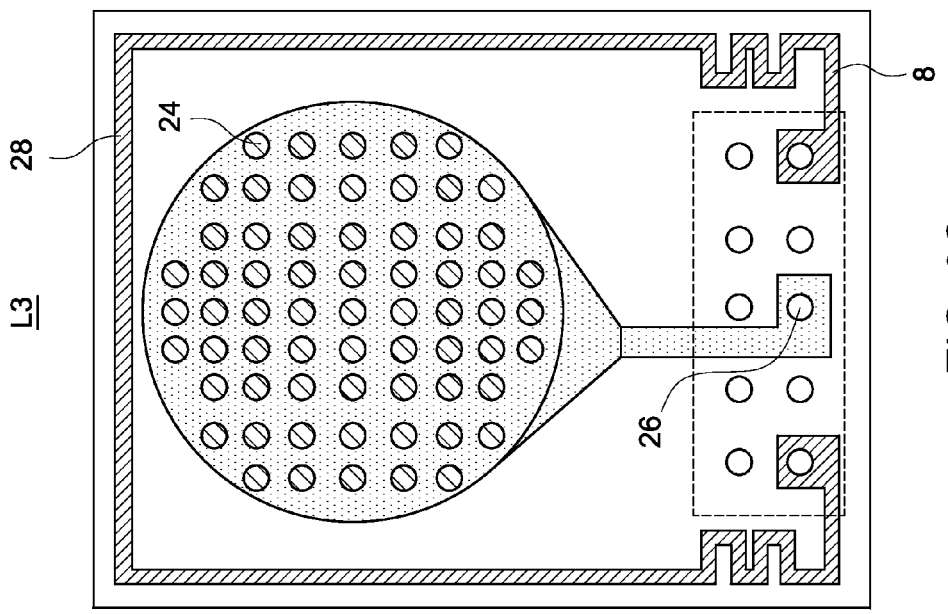
FIG. 6D
FIG. 6C

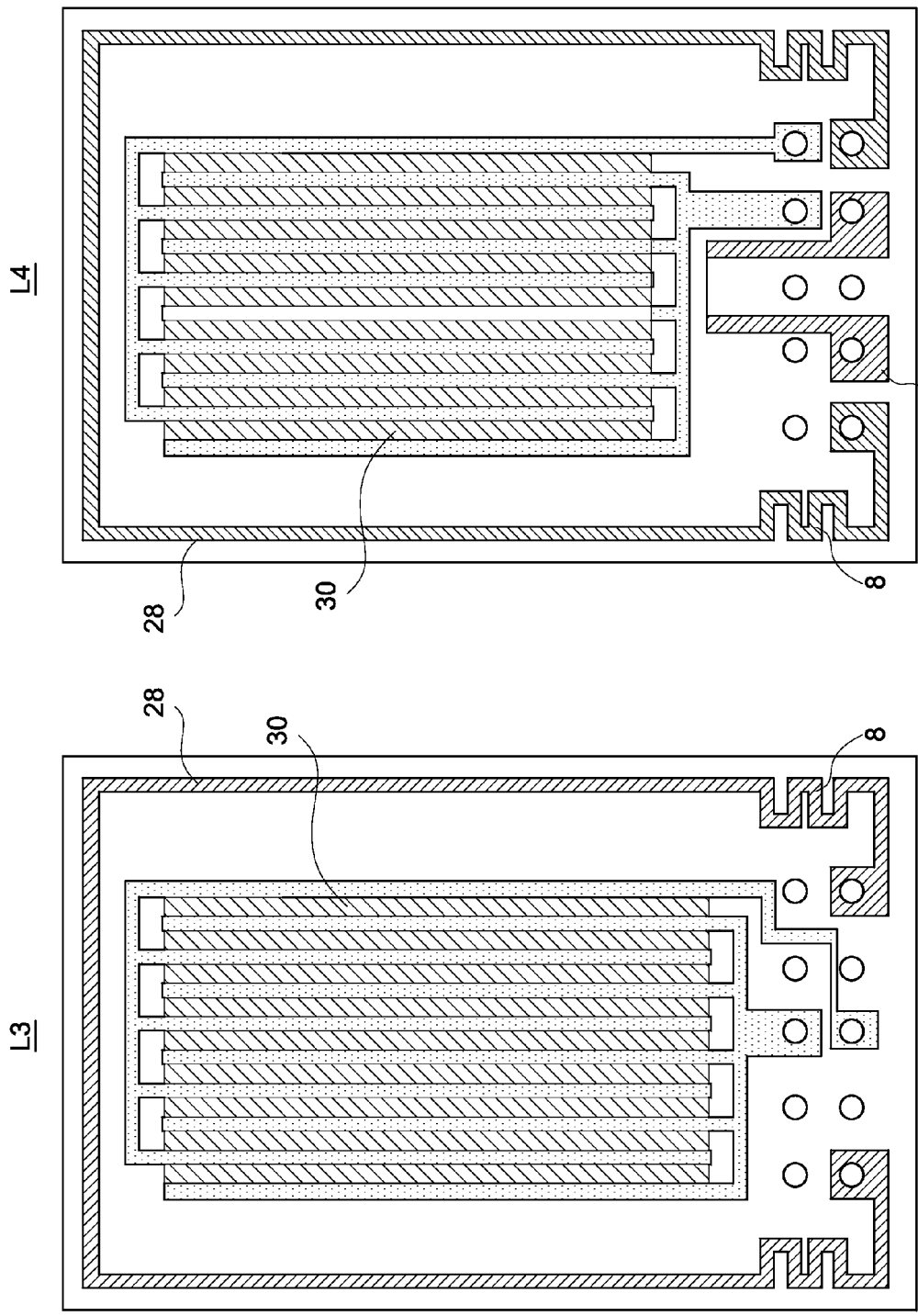

PHOTO-IONIZATION DETECTORS AND ASSOCIATED METHODS THEREOF

FIELD

The invention relates to volatile gas detectors and methods for detecting volatile gas components in breath, and more particularly to photo-ionization detectors and methods for detecting volatile gas components in breath using photo-ionization detectors.

BACKGROUND

The volatile gas components present in a breath of an individual may reveal a health condition of the individual. For example, patients having diabetes, renal failure, or high cholesterol may have high concentrations of acetone, ammonia, or isoprene respectively in their breath. The reactive oxygen species oxidize polyunsaturated fatty acids, excreting lipid-based free radicals and eventually volatile alkanes and methylated alkanes in breath as markers for oxidative stress. Therefore, breath analysis is a way of screening patients for early detection of certain diseases by a reliable, noninvasive, painless, and inexpensive approach. The types and concentrations of chemical compounds that might serve as biomarkers for particular diseases can be determined by various methods, such as gas chromatography, laser spectrometry, ion mobility spectrometry, or sensor technologies such as electrochemical sensor, photo ionization sensor and semiconductor sensor. The latest advancement in breath analysis is to use photo ionization detector (PID) for screening patients having certain diseases.

A typical PID includes an ionization source with high-energy photons, an ionization chamber, and an ion detector. The PID can detect volatile organic gases. In a PID, the high-energy photons are directed to the ionization chamber for collisions with gas molecules, wherein the photons ionize the gas molecules if the energy of the photon is larger than the ionization potential of the molecule. The ionized molecules are electrically detectable as ions and electrons.

Although PID-based sensors may be used to correlate a response signal with a change in ionization, such response signals may be deleteriously affected by other, interfering signals, thereby generating signal artifacts. The signal artifacts may also include unwanted signal responses, for example, responses generated from one or more interfering molecules, such as water, ethanol, or carbon monoxide. The molecules are referred to herein as interfering substances, have high ionization potentials and can block or absorb UV photons, which decrease the detector sensitivity. A concern in prior PIDs is contaminants introduced with the sample and metal atoms released from internal and external electrodes which can deposit on the optical window of the UV lamp forming a coating and reduce the intensity of the UV light from the lamp. The coating reduces the sensitivity of the PID and requires recalibration of the PID using samples of known concentrations of detectable gas. Conventional PIDs also suffer from unstable baseline currents because of metallic electrodes, which are exposed to high-energy photons and release free electrons, which can produce a baseline current flow even when no ionizable gases are present. Frequent calibration of the PID with a reference is needed in order to re-establish a correct baseline current.

Therefore, it is desirable to have a PID sensor, which can detect chemical components in breath with high selectivity and efficiency. The PID is desired to be energy efficient, can be miniaturized for portable applications, does not require frequent calibrations, and has a quick response to change in concentrations of volatile gases in surroundings.

BRIEF DESCRIPTION

The invention relates to PID, and associated sensor systems that are capable of sensing volatile gases present in breath samples, and methods for making and using the sensors. The use of these PID or sensor system resolve the problems associated with the high selectivity and efficiency.

In one embodiment, a photo-ionization detector (PID) comprises a substrate comprising a gas ionization chamber, at least one pair of ion sensing electrodes, and at least one amplifying circuit; and an ultraviolet (UV) ionization source to transmit a UV light beam into the gas ionization chamber.

In another embodiment, a photo-ionization detector (PID) comprises a substrate, comprising a gas ionization chamber, at least one pair of ion sensing electrodes, and a heating element; an ultraviolet (UV) ionization source to transmit a UV light beam into the gas ionization chamber; a temperature sensor; and a temperature feedback control circuit in operative association with the substrate.

In another embodiment, a system for measuring a compound in a gas mixture, comprises a photo-ionization detector (PID), a photo-ionization detector (PID) and a pressure sensor, wherein the PID comprises at least one ultraviolet (UV) ionization source and a substrate comprising a gas ionization chamber, at least one pair of ion sensing electrodes, and at least one amplifying circuit.

In one example of a method of the invention, the method of measuring a compound in a breath sample by a photo-ionization detector (PID) comprises introducing the breath sample into the photo-ionization detector, transmitting an ultraviolet (UV) light beam through the breath sample; ionizing the breath sample; and detecting an amount of the compound in the breath sample.

DRAWINGS

These and other features, aspects, and advantages of the present invention will become better understood when the following detailed description is read with reference to the accompanying drawings in which like characters represent like parts throughout the drawings, wherein:

FIGS. 3A to 3F are schematic drawings of cross-sectional views of substrates having layer-by-layer arrangement.

FIGS. 6A to 6D are schematic drawings of the top view of one example of the PID substrate design comprising the first, second, third and fourth layers respectively with holes.

FIGS. 10A to 10D are schematic drawings of the top view of one example of the PID substrate design comprising the first, second, third and fourth layers with slot openings on a longer integrated circuit board, and including a heater at the second layer.

These and other features, aspects, and advantages of the present invention will become better understood when the following detailed description is read with reference to the accompanying drawings in which like characters represent like parts throughout the drawings, wherein:

DETAILED DESCRIPTION

Figure 1:
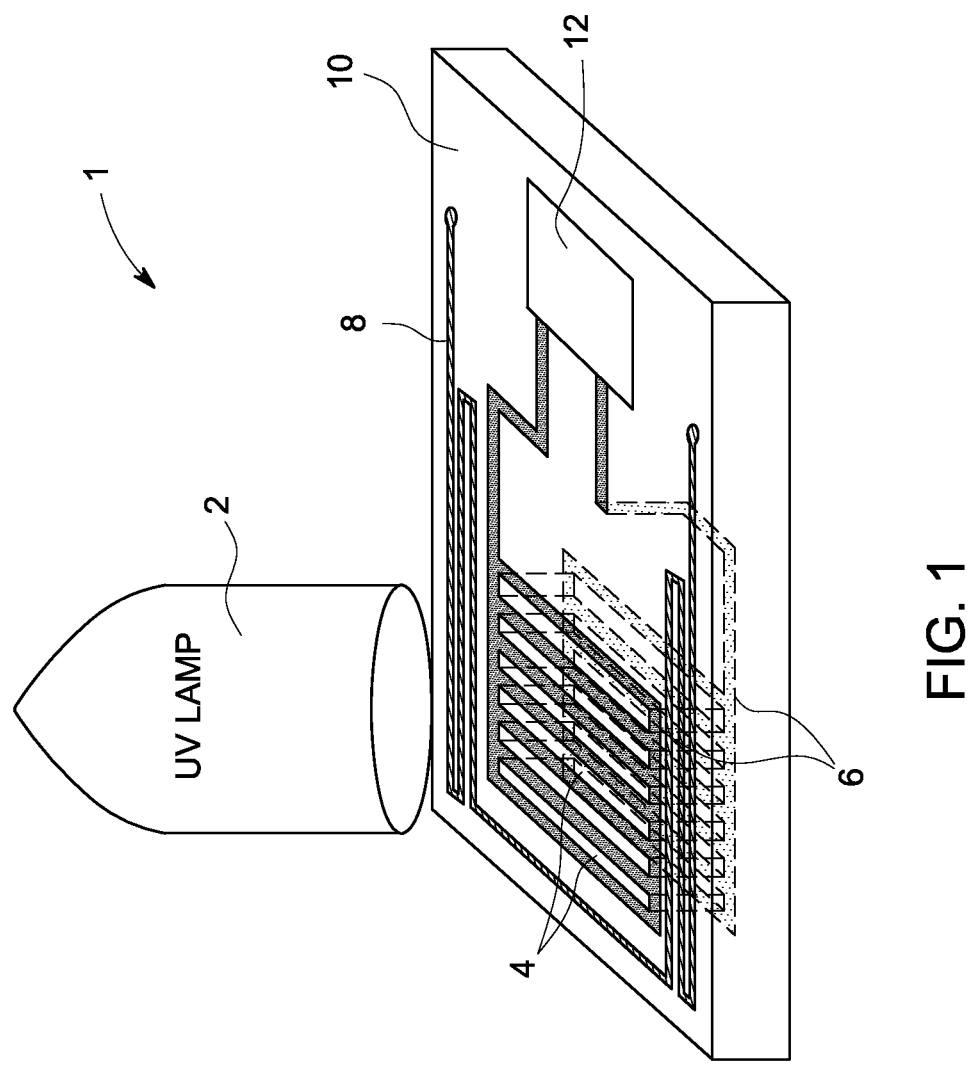
FIG. 1 is a schematic drawing of a top view of a non-limiting embodiment of a photo-ionization detector (PID) of the invention, including an integrated current amplifier.

One or more of the embodiments of the PID are adapted to detect photo ionization of the volatile gases or compounds present in breath. In some embodiments, the PID may be used in a system.

In one or more of the embodiments, the PID comprises a substrate comprising a gas ionization chamber, at least one pair of ion sensing electrodes, and at least one amplifying circuit; and an UV ionization source to transmit a UV light beam into the gas ionization chamber.

The substrate further comprises a heating element. The heating element stabilizes the temperature of the PID and prevents condensation in the PID. The heating element may be a thin film heater, a heating pad, a solid-state heater, a filament heater, a heating tape, or any heater with a heating element. Generally, heating element maintains a nearly constant temperature of the ionization chamber of PID and prevents water condensation from entering gas. In a normal operation, heating element heats ionization chamber up to about 300° C., but any temperature (e.g., 40 to 50° C.) that is above the temperature of the gas entering PID is sufficient to prevent condensation. In the absence of heating element, when PID is cooler than the ambient air, moistures may condense on optical window and electrodes. The condensation on optical window blocks UV light, and the condensation on electrodes causes a leakage current between electrodes. Heating element heats optical window and electrodes in ionization chamber to prevent condensation. In addition, heating element and temperature sensor can maintain PID at an optimal or constant operating temperature through a temperature feedback control loop and eliminate fluctuation of the baseline or zero signal of PID due to temperature variation. In one embodiment, the heating element and the ion sensing electrodes are integrated to the substrate.

The substrate further comprises a temperature sensor. The temperature sensor is useful in sensing change of temperature in the PID. The substrate further comprises a temperature feedback control circuit. The temperature sensor, temperature feedback control circuit and heating element may be present in an operative association, so that when the temperature of PID is different from the desired operation temperature, an error signal is generated based on the temperature sensor's output and a temperature setpoint. The temperature feedback control circuit activates or turn off the heating element based on the error signal to maintain the temperature of the PID to a preset temperature point.

In another embodiment, a PID comprises a substrate, comprising a gas ionization chamber, at least one pair of ion sensing electrodes, and a heating element; an UV ionization source to transmit a UV light beam into the gas ionization chamber; a temperature sensor; and a temperature feedback control circuit in operative association with the substrate. In this embodiment, the PID may further comprise an amplifying circuit.

A pair of electrodes may be disposed on the substrate and may be coupled to the gas ionization chamber. In one embodiment, a pair of electrodes may be disposed on the amplifying circuit and may be coupled to the gas ionization chamber. Non-limiting examples of electrodes may include inter-digitated electrodes, ion sensing electrodes, photoemission electrodes, or discharge electrodes. In some embodiments, two pairs of electrodes may be present. Of the two pairs of electrodes, one pair may be used for measuring the ionized molecules, and the other pair may be used to monitor the photo-emission current. The electrodes of ion detectors may have a variety of shapes. Non-limiting examples of electrode configuration may include interdigitated electrodes, combined electrodes, separated electrodes, parallel plate electrodes, monolayer electrodes, and multilayered electrodes. The multilayered electrode may comprise alternating conducting layers and dielectric layers. In some embodiments of the multi-layered electrode, the electrode is made of plurality of conducting layers, or the electrode is made of plurality of dielectric layers. The substrate may further include one or more electrodes in between a pair of ion sensing electrodes to eliminate substrate current interference. This electrode used in between a pair of ion sensing electrodes, is also refers herein as a fence electrode. The fence electrode prevents ion-leakage between two ion-sensing electrodes.

An interference results from a leakage current between two electrodes is known as 'substrate current interference'. In high voltage, the current leaks from the surface or edge of the electrodes. Two conductors are disposed on an insulating substrate to form the ion sensing electrodes. During sensing operation, a bias voltage is applied between the two electrodes to measure ion current (used herein as ion current measuring electrodes) of the gas sample. However, a leakage current may flow through the surface of the insulating substrate. The leakage current causes interference to the ion current. One method to reduce the leakage current is by using a third electrode in between the two ion sensing electrodes. By connecting the third electrode to ground or to a specific voltage source, leakage current may flow through the third electrode to the ground or to the specific voltage source instead of reaching the two measuring electrodes.

The ion sensing electrodes attract positive ions formed when UV photons impact the ionizable gas molecules. An electrometer is present in operative association with the ion sensing electrodes. The ion sensing electrodes measure the ion current and the electrometer converts the ion current to a voltage, which is directly proportional to the concentration of ions. The concentration of the ions provides a measurement of equivalent amount of compounds present in the gas sample. The UV photons impact the photoemission electrode, which may liberate electrons but those electrons are typically attracted back to the photoemission electrode and do not contribute to a baseline current between the ion sensing electrodes. The photoemission electrode measures the electron number, which indicates the conditions of UV lamp.

The substrate is made of one or more conducting layers, dielectric layers, or combinations of conducting layers and dielectric layers. The substrate is made of metal, ceramic, glass, polymer, or combinations thereof. In one embodiment, the substrate is made of semiconductor materials selected from the group consisting of silicon, germanium, silicon carbide, silicon nitride, aluminium nitride, aluminium phosphide, boron nitride, boron phosphide, and combinations thereof. The substrate may be, for example, a ceramic substrate, a printed circuit board, or a silicon substrate. The ceramic-based multilayer substrate may be formed by low temperature co-firing ceramic technology. In one embodiment, the substrate is a printed circuit board. Conducting layer deposition and patterning on the top surface of the substrate may form ion-sensing electrodes. The heating element may present on the top surface of the substrate, or on the bottom surface of the substrate. In one embodiment, the conducting layer of the substrate may function as the heating element.

The substrate may be single layered, or multilayered. The multilayered substrate may comprise alternating conducting layers and dielectric (or non-conductive) layers. In some embodiments of the multilayered substrate comprise a plurality of conducting layers, or plurality of dielectric layers. The multilayered substrate may comprise a first layer, a second layer, a third layer, and a fourth layer. In a non-limiting embodiment, the substrate may comprise more than four layers. In one embodiment, the first layer of the substrate may comprise at least a pair of ion sensing electrodes, an amplification circuit, and at least one ionization chamber. The second layer of the substrate may comprise a pair of electrode connecting to the UV lamp, and a lamp holder that holds the UV lamp, which is connected to the substrate. In another embodiment, the first layer of the substrate may further comprise a heating element on the substrate. The first layer of the substrate may comprise a temperature sensor on the substrate. In some other embodiments, the second layer of the substrate may comprise a heating element and a temperature sensor on the substrate. The multilayered substrate may have one or more gaps or channels in between two or more conducting layers. The ionization chamber may form in one or more gaps or channels in between two dielectric layers on the substrate.

The substrate comprises an array of holes or open slots. The holes or open slots provide open spaces to ionize the molecules, and configured as a gas ionization chamber. The holes or open slots are also function as connecting pins between various layers. The open slots are mainly rectangular in shape. In some embodiments, the substrate may comprise a plurality of layers, wherein the top and the bottom layers have holes or slot openings. In those embodiments, the middle layers have void spaces, which form a chamber for gas ionization. The gas passes through the holes or slot openings to the void spaces and UV light beam passes through the gas in perpendicular direction, which results ionization of the gas molecules. The gas ionization chamber may comprise ion-sensing electrodes to determine ion current. The gas ionization chamber further comprises a diffuser that regulates a controlled gas flow into the gas ionization chamber.

The UV ionization source is an ultraviolet lamp (UV lamp), or a light emitting diode (LED). In one embodiment, the UV ionization source is directly fixed on the lamp driver board. The UV ionization source transmits UV light in a frequency range from about 100 nm to 210 nm. When an external electrical field excites the UV lamp, a UV radiation is produced, wherein the UV radiation may be in the form of a UV light beam. The UV light beam is directed into the gas ionization chamber perpendicular to a path of gas flow. In some embodiments, the UV ionization source is directly fixed to the substrate. In some embodiments, multiple UV lamps may be use to provide selectivity for various compounds present in the breath sample. Different compounds in breath have varying PID potentials therefore providing intrinsic selectivity by using low energy UV lamp, and/or using combinations of different UV lamps. The UV ionization source can selectively provide UV lights of more than one energy levels. The UV ionization source is selected from the UV lamp of 8.4 eV, 9.6 eV, 9.8 eV, 10 eV, 10.2 eV, 10.6 eV or 11.6 eV or a combination of more than one foregoing UV lamps. Different gas has different emission wavelengths, hence, different ionization energy. Typical inert gases used for UV lamp are krypton, xenon, and argon. For example, the krypton has ionization energy in a range from about 10 to 10.6 eV, xenon has ionization energy in a range from about 8.4 to 9.6 eV, and argon has ionization energy of 11.7 eV.

A conventional gas discharge UV lamp for a PID is a sealed glass envelope containing two plates. A high voltage, which is applied to the plates via the leads that extend from the plates out of the glass envelope, causes a glow discharge process in a gas, which is trapped in the envelope. The glow discharge process generates UV photons that exit the envelope through an optical window and illuminate the ionization chamber of the PID.

The UV ionization source ionizes the gas in the ionization chamber, and the ions are measured by ion sensing electrodes and generate a response signal. The response signal may be generated due to a change in ion concentrations on ion sensing electrodes and the response signal is detectable with respect to control. The extent of ionizations of various compounds is different with respect to ionization energy, and the ionization of the compounds generates ions, which result a response signal that represents different compounds.

The PID further comprises a direct current (DC) voltage source. The DC voltage source generates a high voltage to the ion sensing electrodes. The ion sensing electrodes are connected to a high voltage DC source that provides a DC voltage of 10-200 V.

A typical PID senses ions and generate a signal outputs on the order of pico-amperes to microamperes. In order to achieve accurate measurement of the small current, a current amplifier is used to amplify the signal to a large enough voltage signal, which may be recorded. The PID comprises at least one amplifying circuit, which amplifies the response signal generated by ion sensing electrodes to form amplified signals. The amplified signals are transmitted to a processor, wherein the processor may be present in operative association with the PID. The at least one amplifying circuit is selected from a transimpedance amplifying circuit, or a current-to-current amplifying circuit. A transimpedance amplifier converts current to voltage and amplify the signal. One way to make a transimpedance amplifier is to use a high gain operational amplifier with a resistive feedback. The feedback resistor determines the transimpedance gain. The bias voltage, such as $Vb1$ impact on the positive terminal of the operational amplifier and determines the baseline output voltage. In high sensitivity applications, a guard ring may be added to reduce stray leakage current from corrupting the signal going into the amplifier.

The substrate may have a filtering circuit. The filtering circuit may reduce the measurement noise. The noise may be generated with the signal by substrate current interference, temperature variation, humidity interference, electromagnetic interference, capacitive coupling, inductive coupling, or other electrochemical interferences. To reduce the substrate current interference, one electrode of a pair of electrodes is attached to the ground or a voltage source, wherein the electrode eliminates the leakage current. A variation in temperature may generate a temperature-induced noise, which can be eliminated by using a temperature feedback control circuit. Using a heating element, the humidity-induced noise may be eliminated. The heating element maintains the inside temperature of the PID and reduce the condensation. Packaging the PID inside a metal shield may eliminate electromagnetic interference. Amplifier is used to minimize noise generated from capacitive coupling or inductive coupling. Positioning of amplifier in a close proximity of the ion sensing electrodes may reduce electrochemical or other interferences. When measuring low concentration target molecule in the sub ppb to ppm range, the ion current is very small. Any measurement noise or interference may affect the measurement of such small current. One method to reduce noise or interference is to have the amplifying circuit in close proximity of the ion sensing electrodes, which minimizes the coupling noise and interference. A significant noise reduction may generate a prominent and clear signal, which may provide an accurate measurement of ionized molecules of various compounds.

The PID detects chemical compounds, volatile gases, or volatile organic compounds (VOCs) present in a gas mixture. For example, PID detects chemical compounds, volatile gases, or volatile organic compounds (VOCs) present in a breath sample. The PID is configured to detect aliphatic hydrocarbons, aromatic hydrocarbons, aldehydes, ketones, or alcohols. The PID is configured to detect acetone, isoprene, ammonia, ethanol, methanol, ethane, pentane or benzene. In a specific embodiment, the PID is configured to detect acetone. For selective detection of compounds in breath using PID, a combination of different UV lamps may be used while subtracting or compensating the contributions of interference of other compounds. The sampling method may be implemented such that only certain compounds are collected and introduced to PID detector to prevent interferences. The sampling method can be membrane based, pre-concentrator trap based, or other type of separation method, such as gas chromatography, or gas filters, however, some kinds of semi-separation method might also be useful. For example of a pre-concentrator trap based method, acetone can be trapped by Carbotrap X but larger molecules will not be trapped by this material. A different scenario can be that the analyte of interest may flow through the selected preconcentrator trap without being retained while most other interferents get trapped. For example, acetone will pass through the Carbotrap Y and Carbotrap B, which can trap a wide range of VOCs having carbon chain length from C5-C20.

A system for measuring a compound in a gas mixture comprises a PID, and a pressure sensor. The system further comprises a processor configured to produce a sensor response pattern that indicates an amount of the compound in the gas mixture. The PID comprises a substrate, and an UV ionization source to transmit a UV light beam into the gas ionization chamber. The substrate comprises a gas ionization chamber, at least one pair of ion sensing electrodes, and at least one amplifying circuit. In an alternate embodiment, the system for measuring a compound in a gas mixture comprises a PID, a pressure sensor, and a processor, wherein the PID comprises a substrate. The substrate comprises an UV ionization source to transmit a UV light beam into the gas ionization chamber, a temperature sensor, and a temperature feedback control circuit in operative association with the substrate. In this embodiment, the substrate comprises a gas ionization chamber, at least one pair of ion sensing electrodes, and at least one heating element.

An absolute pressure sensor with a pressure measuring range of 0-30 inch-water is used to measure pressure of breath sample. The use of pressure sensor ensures that the breath sample subjected to the PID has a proper blowing pattern with a constant pressure. A constant pressure is desirable during the measurement to generate accurate data. A differential pressure sensor with a range of 0-1 inch-water is used to measure the flow rate of breath sample based on differential pressure measurement at two locations in the PID. The purpose of the flow measurement is to ensure providing enough volume of breath to the PID for an accurate measurement. Typically, only the end tidal breath contains the right ion concentration, which may be captured by monitoring the flow rate of breath sample and PID signal after passing certain volume of breath sample. Depending on the age, physical condition, and other related parameters of the user, the initial dead volume of breath sample may be different. The system further comprises a diffuser that regulates a flow of the gas mixture. The diffuser is coupled to the gas ionization chamber. The at least one pair of ion sensing electrodes is an acetone sensing electrodes. The system further comprises a gas flow-rate sensor. The gas flow-rate sensor is configured to detect flow rate of gas while passing through gas ionization chamber.

The system further comprises a $CO_2$ sensor. $CO_2$ measurement is an important aspect of breath analysis. The level of $CO_2$ concentration determines various parameters in the system. For example, $CO_2$ concentration determines whether the user breath may reach the end-tidal of the system. Desired $CO_2$ concentration for end-tidal breath is around 5%. Therefore, a $CO_2$ sensor may ensure the accurate end-tidal measurement. The second purpose for using $CO_2$ sensor is to provide a normalization parameter to compare measured data between different subjects. Various subjects (human individual) have different metabolic rate and respiratory ventilation rate, resulting in different VOC concentration in breath. Therefore, it is hard to compare absolute VOC concentration data. However, if the concentration is normalized by breath $CO_2$ concentration, then a comparison may be established in a large-scale database for breath analysis application.

The system further comprises a controller, which is present in operative association with the PID. The controller mainly regulates the temperature feedback control unit, and the heating element depending on the temperature of the PID. The controller also controls the system by using heating element to reduce humidity and condensation.

A method of measuring a compound in a breath sample by a PID, comprises collecting the breath sample; introducing the breath sample into the PID, transmitting an UV light beam through the breath sample, ionizing the breath sample, and detecting an amount of the compound in the breath sample. The method further generates a sensor response pattern. The sensor response pattern quantifies the amount of each compound present in the breath sample. The method further comprises heating the photo-ionization detector by using a heating element for maintaining a temperature inside the PID. The method further comprises measuring a temperature of the PID by a temperature sensor present in the PID. The method further controls a temperature-feedback control mechanism using the temperature sensor and the heating element.

Figure 2:
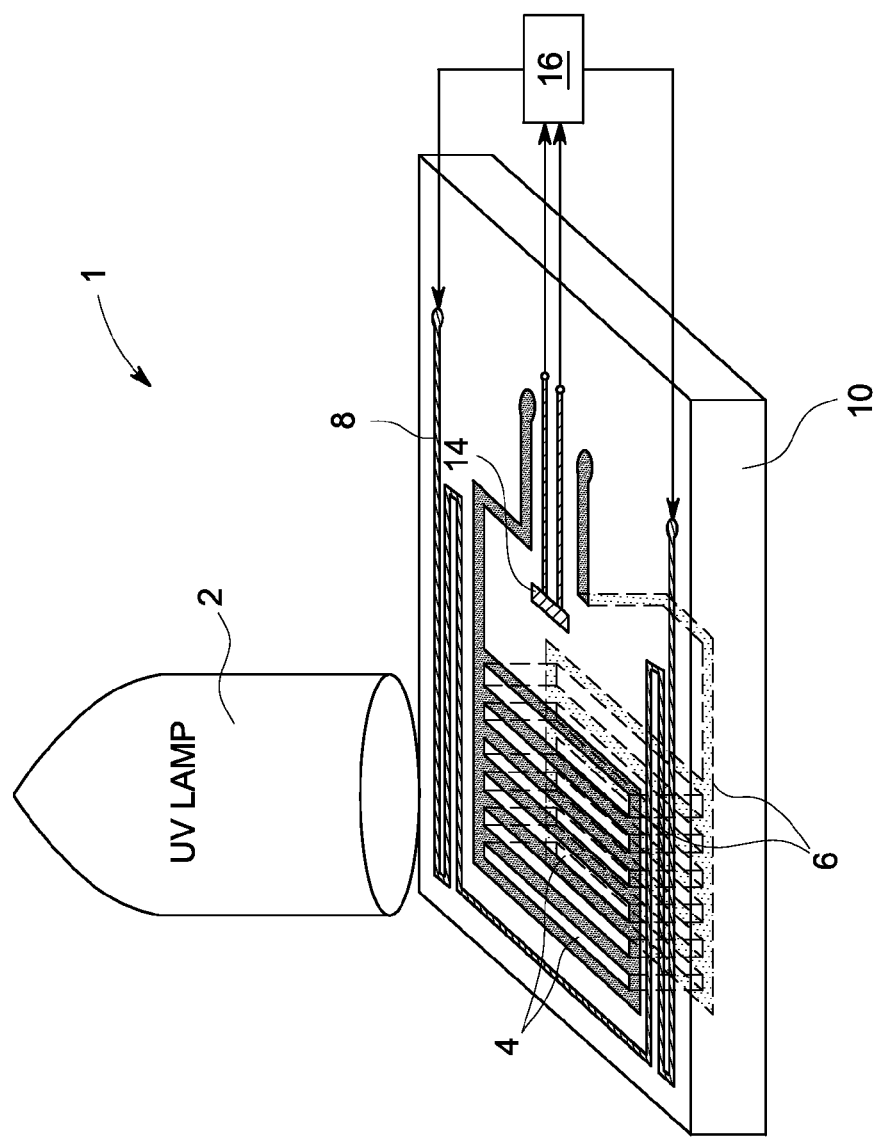
FIG. 2 is a schematic drawing of a top view of a non-limiting embodiment of a PID of the invention, including an integrated heater and temperature sensor.

Referring now to FIG. 1 and FIG. 2, two different embodiments of a PID sensor 1 are illustrated. The PID sensor 1 employs an integrated substrate structure 10 including the ionization chamber 4, ion sensing electrodes of PID 6, and heating element 8. In one embodiment, the substrate 10 is made of ceramic, with a thickness of at least 0.1 mm. The PID comprises an ultraviolet (UV) ionization source 2 to transmit a UV light beam into the gas ionization chamber. In the embodiment of FIG. 1, the PID comprises an amplifier or an amplifying circuit 12. In the embodiment of FIG. 2, the PID comprises a temperature sensor 14, and a temperature feedback control unit 16.

Figure 3E:
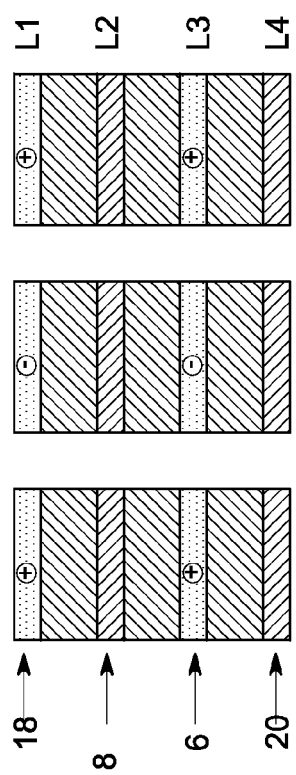
Figure 3F:
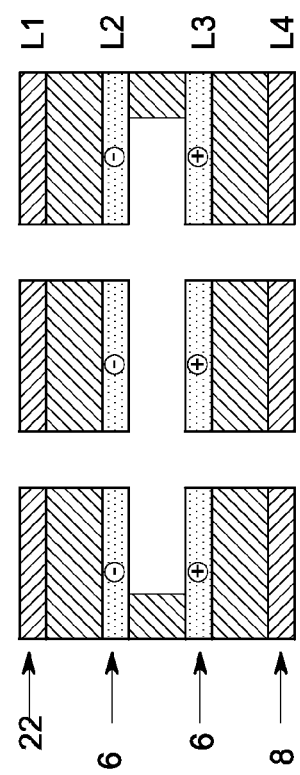

FIGS. 3A to 3F illustrate cross-sectional view of a layer-by-layer arrangement of the substrate 10. An example of a substrate comprises four conductive layers and three non-conductive layers. The first, second, third, and fourth conductive layers are designated as L1, L2, L3, and L4 respectively. The 4 conductive layers are electrically insulated by 3 non-conductive layers. In FIG. 3A, L1 and L3 comprise ion-sensing electrodes 6, wherein an intervening layer L2 is present that comprises a fence electrode 20. The fence electrode 20 prevents leakage of current between ion sensing electrodes. The L4 comprises heating element or heater 8. In FIG. 3B, L1 and L3 are ion-sensing electrodes 6, wherein an intervening layer L2 is present as a fence electrode 20. The L4 comprises a temperature sensor 22. In FIG. 3C, L1 and L2 comprise UV monitor 18, L3 and L4 comprise ion-sensing electrodes 6, and L4 further comprises a temperature sensor 22. In FIG. 3D, L1 comprises an UV monitor 18, L2 and L4 comprise ion-sensing electrodes 6, wherein an intervening layer L3 comprises a heating element 8. In FIG. 3E, L1 comprises an UV monitor 18, L2 comprises a heating element 8, L3 comprises an ion-sensing electrode 6, and L4 comprises a temperature sensor 22. FIG. 3F is a cross-section view of one detector design, in which, the first conductor layer L1 is used as temperature sensor 22, the second layer L2 and third layer L3 are used as ion detector 6, and the fourth layer L4 is used as a heating element 8.

Figure 4B:
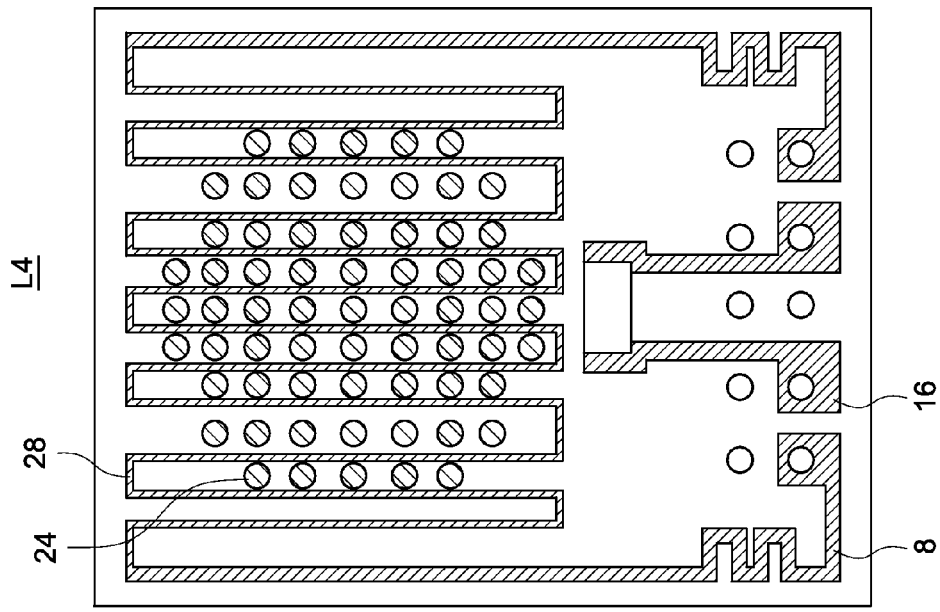
FIG. 4B is a schematic drawing of the top view of the same PID substrate design comprising the fourth layer with holes.
Figure 4A:
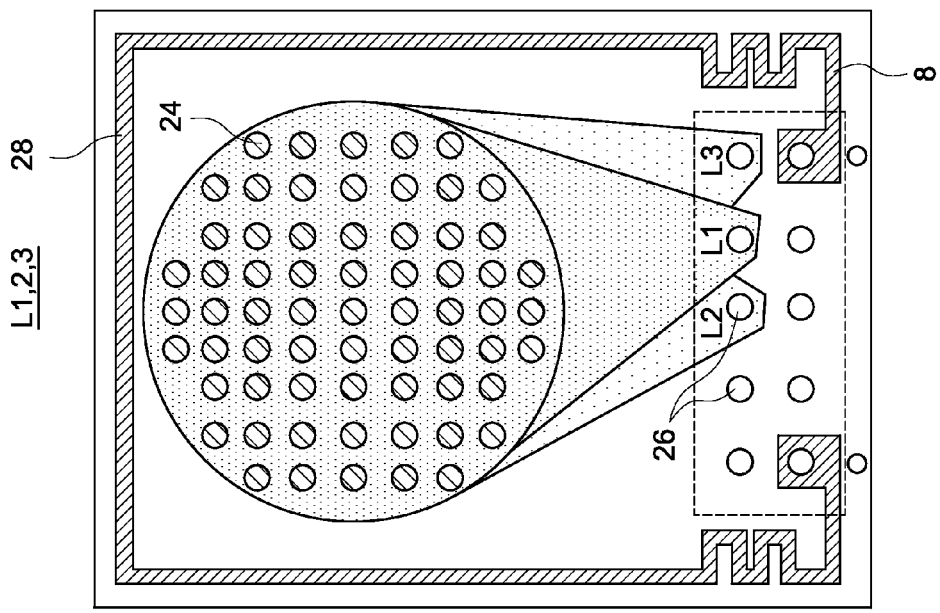
FIG. 4A is a schematic drawing of the top view of one example of the PID substrate design comprising the first, second, and third layers with holes.

FIGS. 4A and 4B are top view of the PID 1 having substrate with holes. The PID comprises an integrated circuit board 28. The layers of the substrate 10 are inter-connected to each other by holes 24 as shown in FIGS. 4A and 4B. The size of the hole is in a range of about 0.1 to 1 mm. A distance between edges of any of the two holes is 0.1 to 0.5 mm. In a specific embodiment, the distance between edges of any of the two holes is 0.3 mm. Each of the layers comprises one or more connecting pins 26. FIG. 4A shows three layers, L1, L2, and L3, wherein the heating elements or heaters are present on all three layers L1, L2, L3, and the heating elements are connected in series through holes. The heating element has a long serpentine design, and the length may be about 1 m. FIG. 4B shows the layer L4, which comprises heating element 8, and a temperature feedback control circuit 16.

Figure 5B:
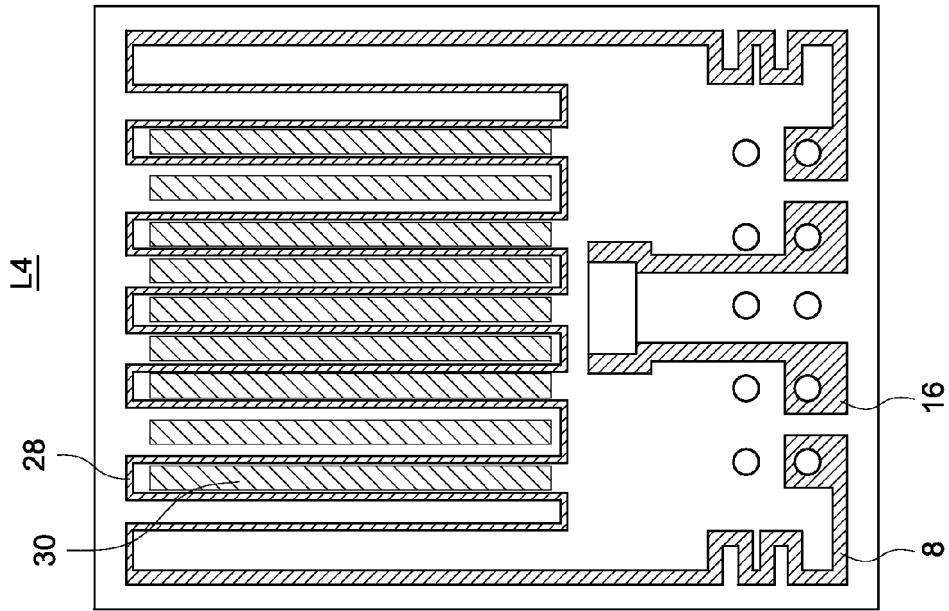
FIG. 5B is the top view of the same PID substrate design comprising the fourth layer with slot openings.
Figure 5A:
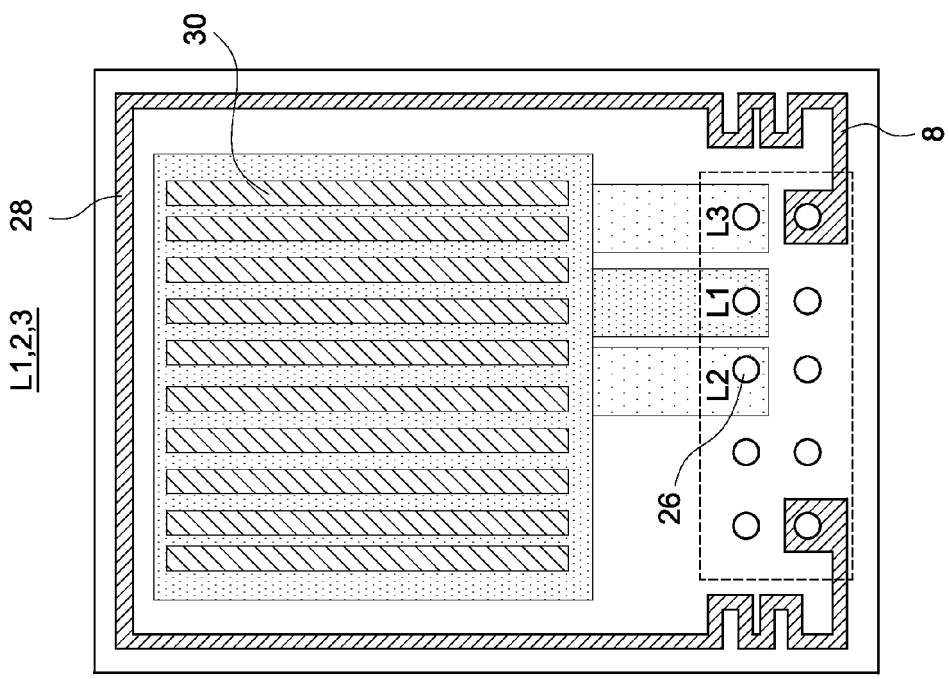
FIG. 5A is a schematic drawing of the top view of one example of the PID substrate design comprising the first, second, and third layers with slot openings.

FIGS. 5A and 5B are top view of the PID 1 having substrate with slot openings. In one example, the slots are rectangular in shape. The PID comprises an integrated circuit board 28. The layers of the substrate are inter-connected to each other by slot openings 30 as shown in FIGS. 5A and 5B. In one example, each of the slots has a length of 8 mm. In a specific embodiment, the distance between an edge of the slot and the edge of the integrated circuit board is about 2 mm. Each of the layers comprises one or more connecting pins 26. The PID comprises an integrated circuit board 28, which has a length of 16 mm and width of 12 mm. FIG. 5A shows three layers, L1, L2, and L3, wherein the heating elements or heaters are present on all three layers L1, L2, L3, and the heating elements are connected in series through layer interconnects. FIG. 5B shows the layer L4 comprising heating element 8, and the temperature feedback control circuit 16.

Figure 6B:
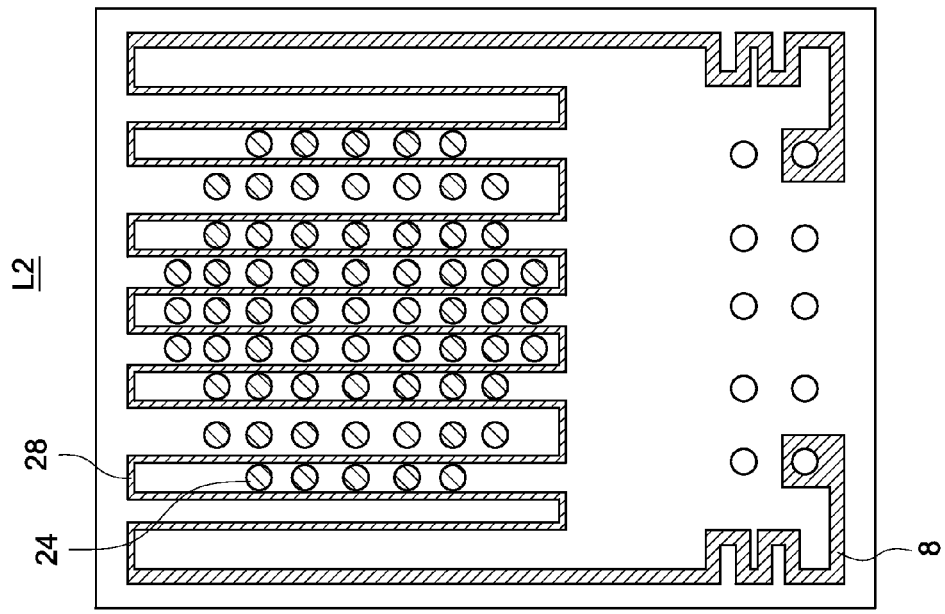
Figure 6A:
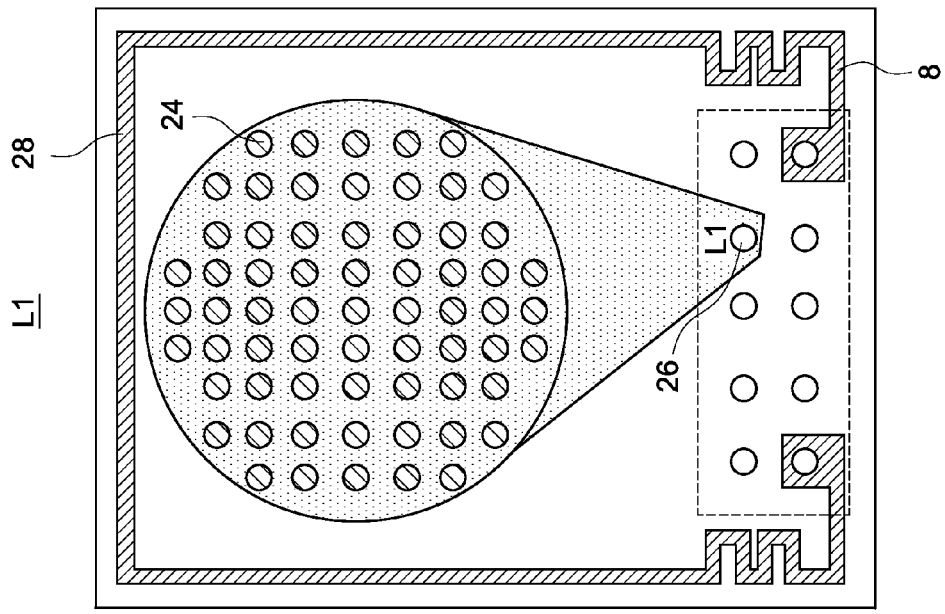

FIGS. 6A to 6D are top view of the PID 1 comprising an integrated circuit board 28 with holes. The layers of the substrate are inter-connected to each other by holes 24. Each of the layers comprises one or more connecting pins 26. FIG. 6A, 6B, 6C, and 6D illustrate four different layers L1, L2, L3 and L4 respectively, wherein the heating elements or heaters are present on all four layers and the heating elements are connected in series through layer interconnects. FIG. 6D shows the layer L4, which further comprises the temperature feedback control circuit 16. Similar designs also exist with slot openings.

Figure 7B:
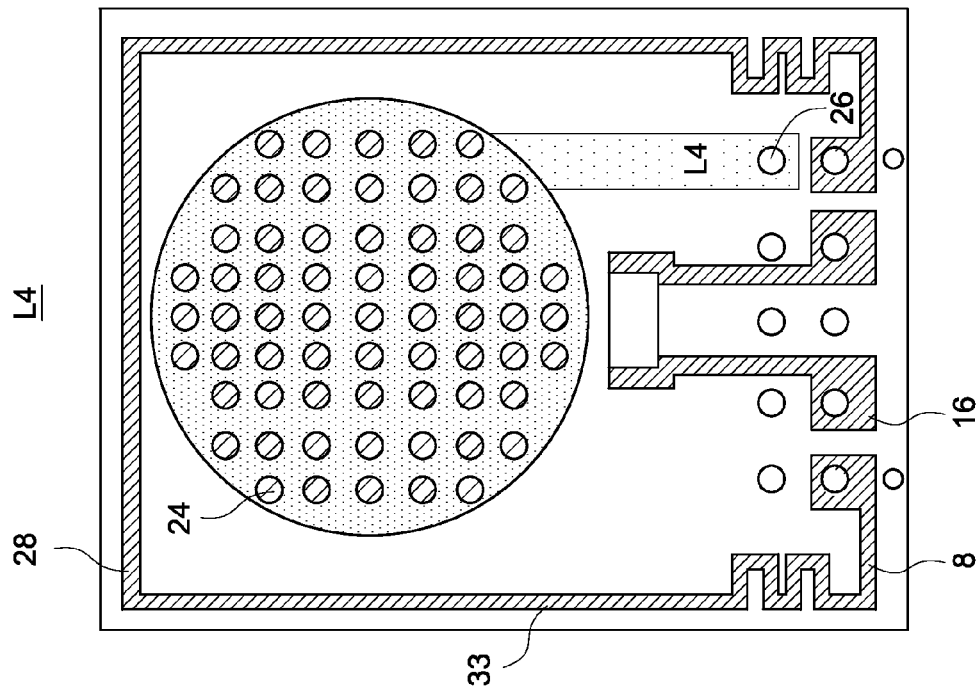
FIG. 7B is a schematic drawing of the top view of the same PID substrate design comprising the fourth layer with ion sensing electrodes stacked together.
Figure 7A:
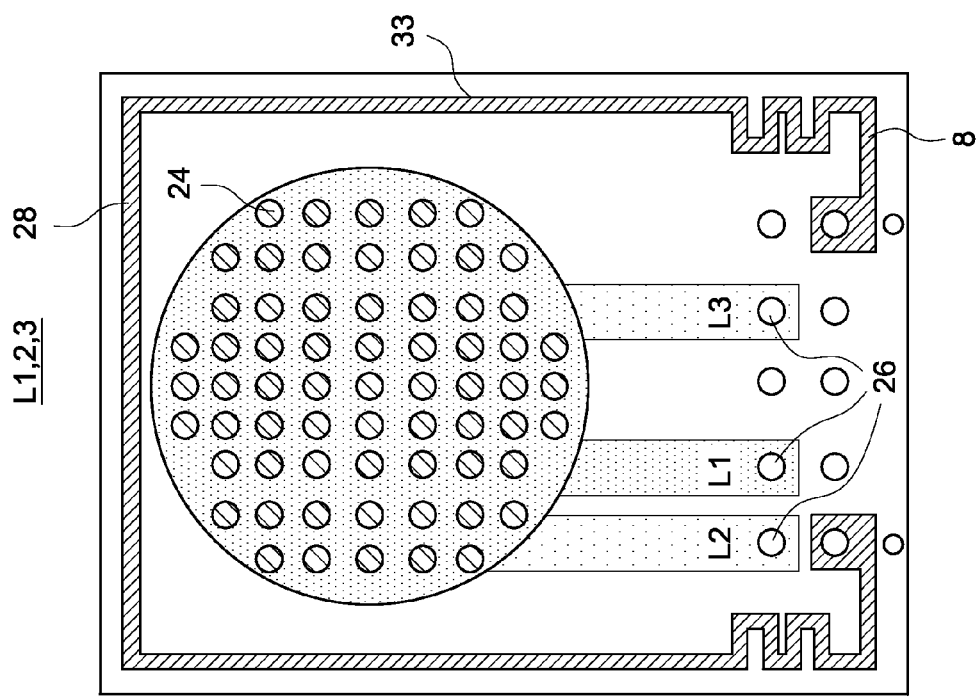
FIG. 7A is a schematic drawing of the top view of one example of the PID substrate design comprising the first, second, and third layer with ion sensing electrodes stacked together.

FIGS. 7A and 7B are top view of the PID 1 comprising an integrated circuit board 28 with holes. FIG. 7A shows three layers, L1, L2, and L3, wherein the heating elements or heaters are present on all three layers L1, L2, L3, and the heating elements are connected in series through layer interconnects. The heating element has a long serpentine design, and the length may be about 1 m. FIG. 7B shows the layer L4, which comprises heating element 8, and the temperature feedback control circuit 16. Similar designs also exist with slot openings.

Figure 8B:
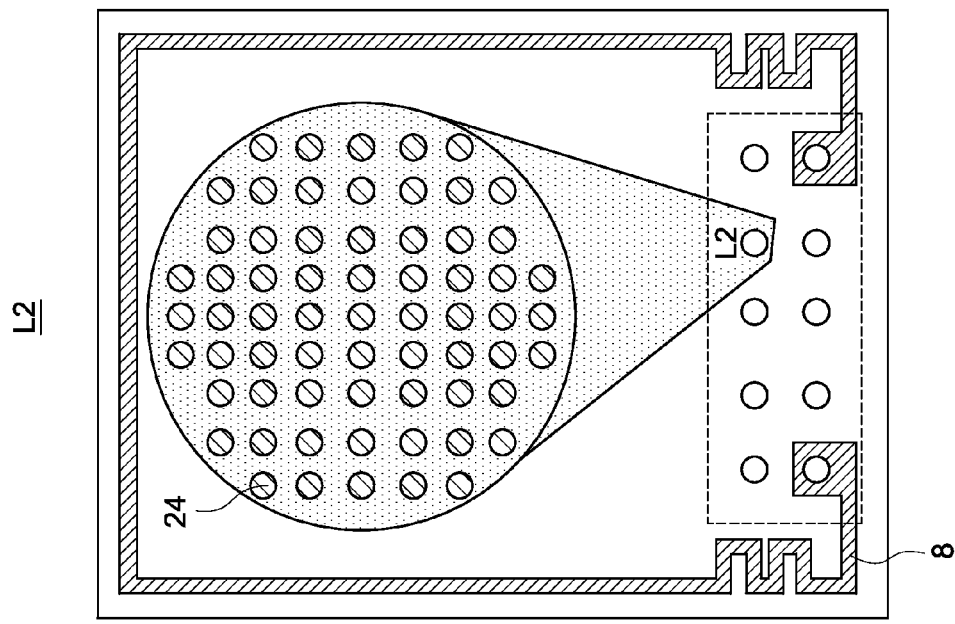
FIGS. 8A to 8D are schematic drawings of the top view of one example of the PID substrate design comprising the first, second, third and fourth layers with holes, and including a heater that functions as a fence electrode.
Figure 8A:
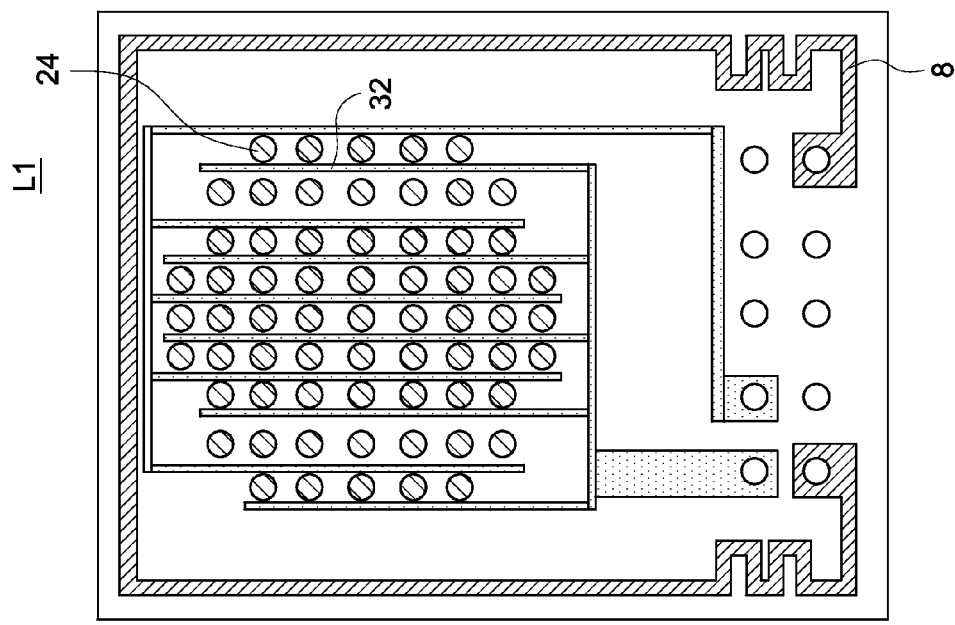
Figure 8D:
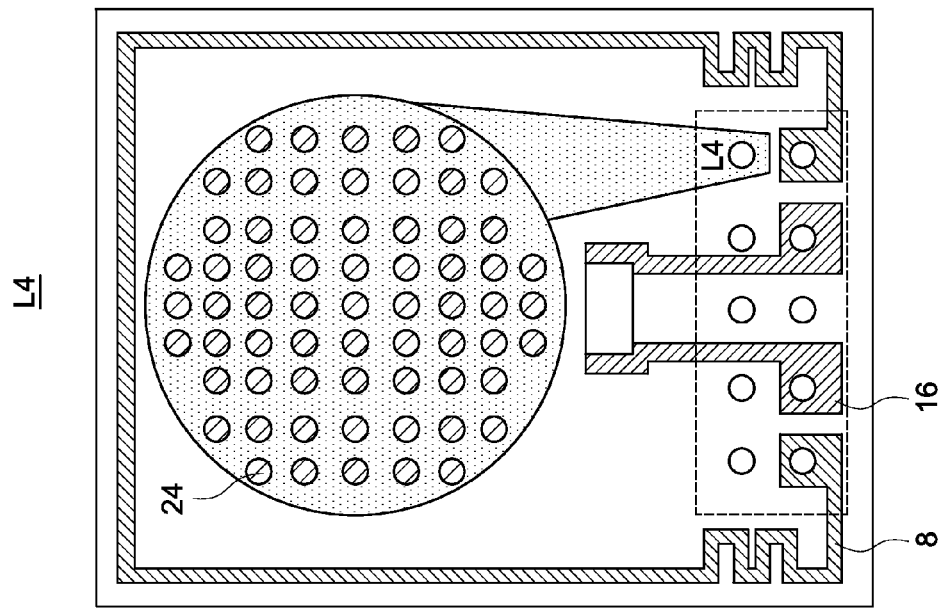
Figure 8C:
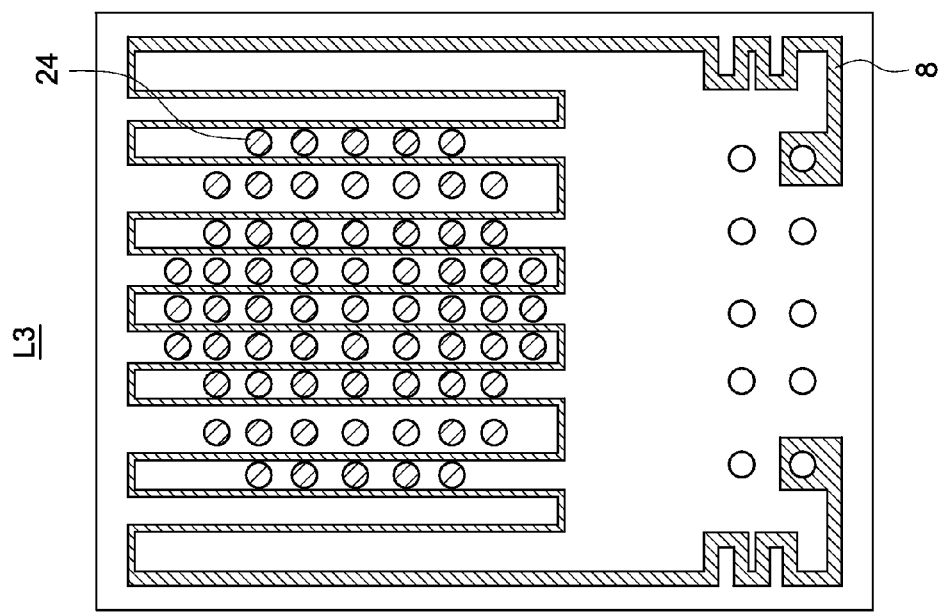
Figure 9B:
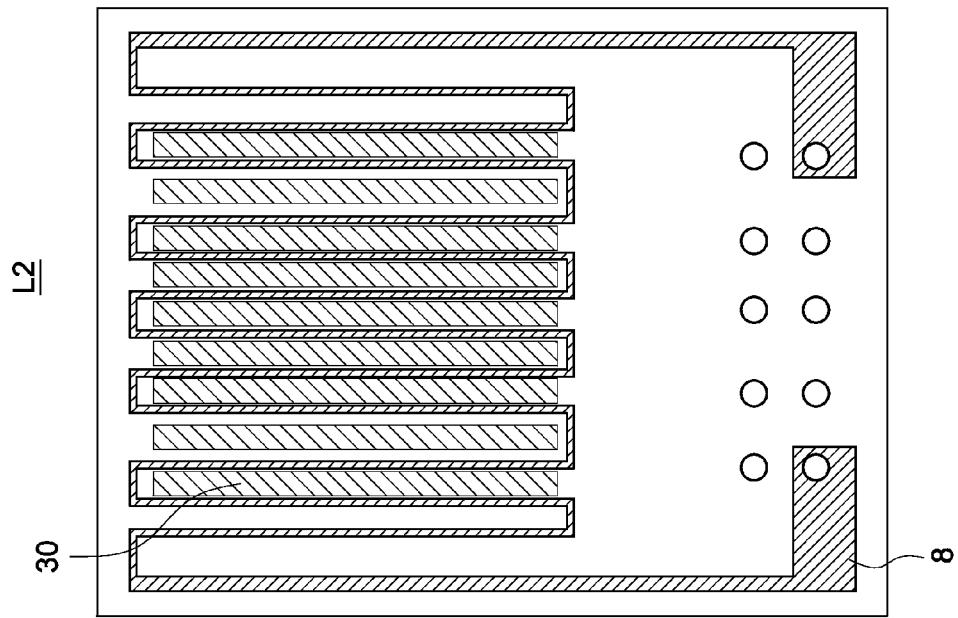
FIGS. 9A to 9D are schematic drawings of the top view of one example of the PID substrate design comprising the first, second, third and fourth layers with slot openings, and including a heater that functions as a fence electrode.
Figure 9A:
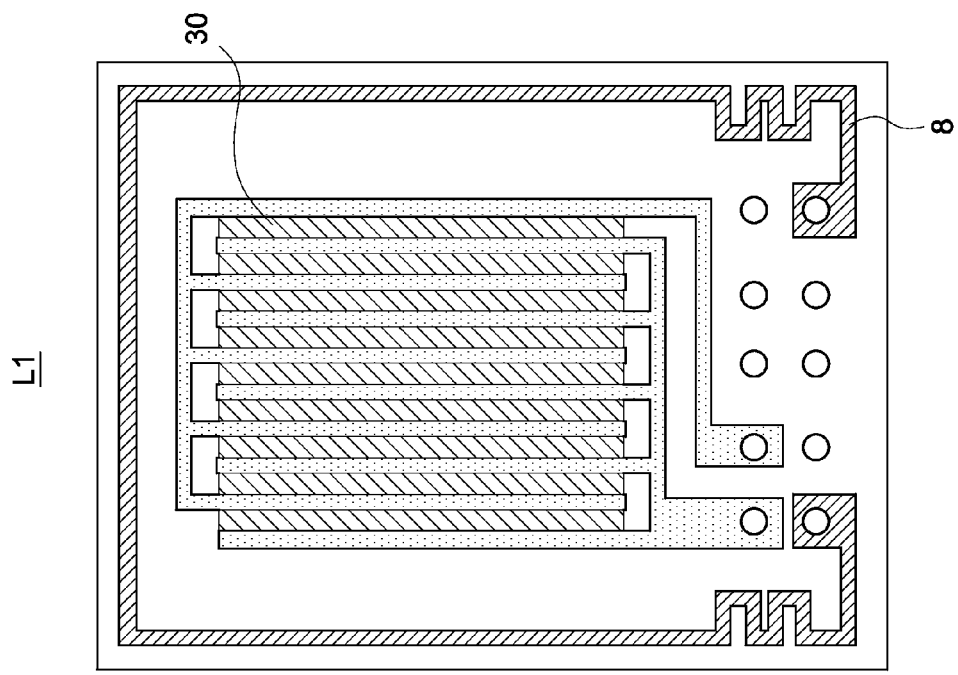
Figure 9D:
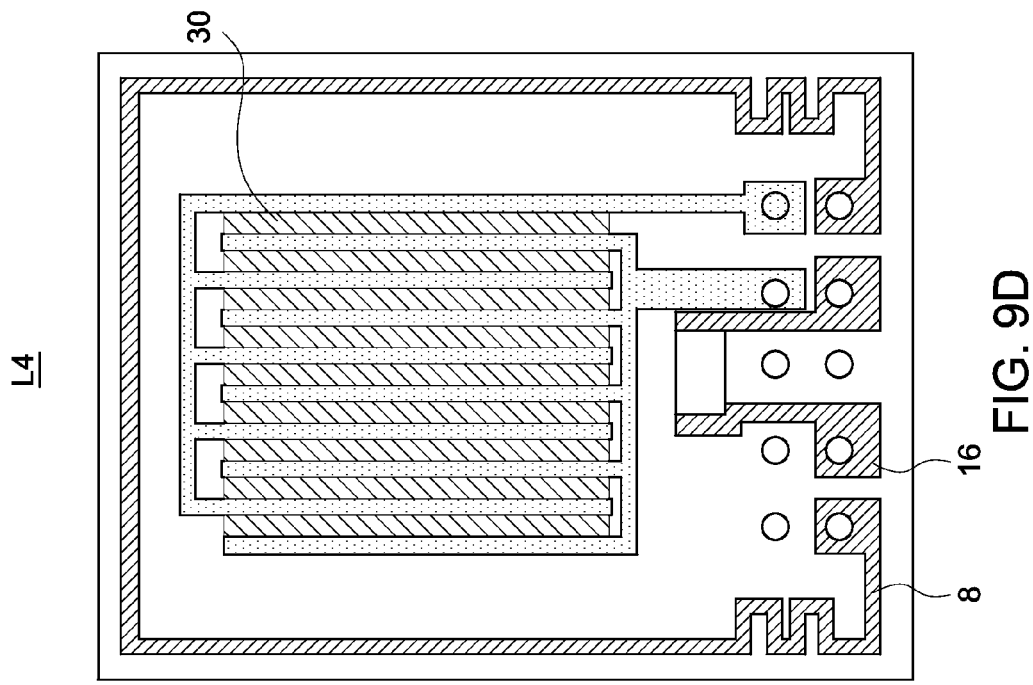
Figure 9C:
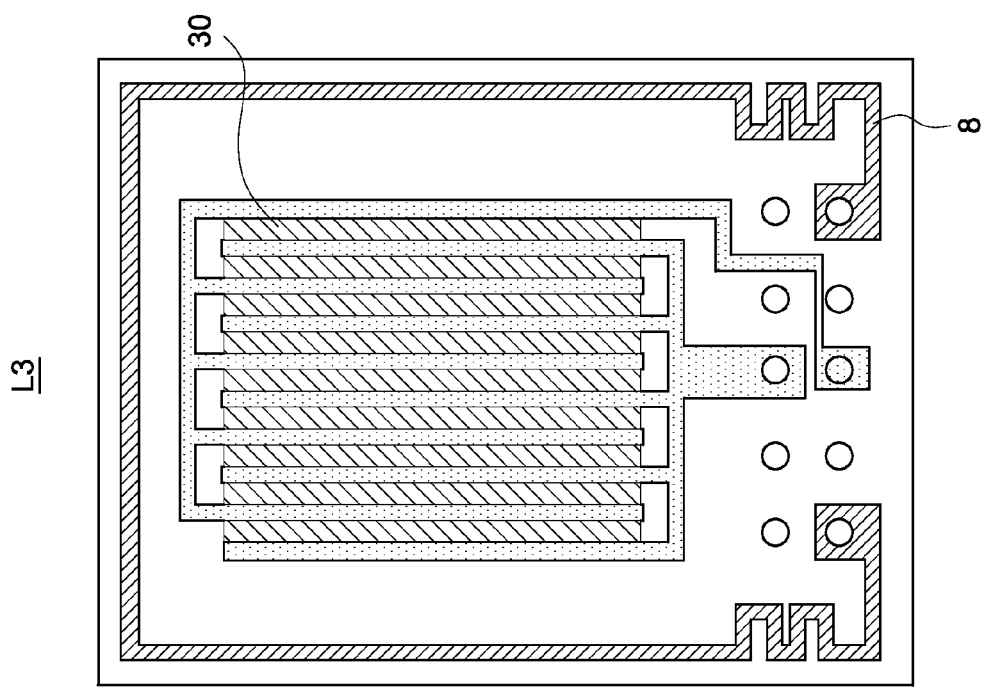
Figure 10A:
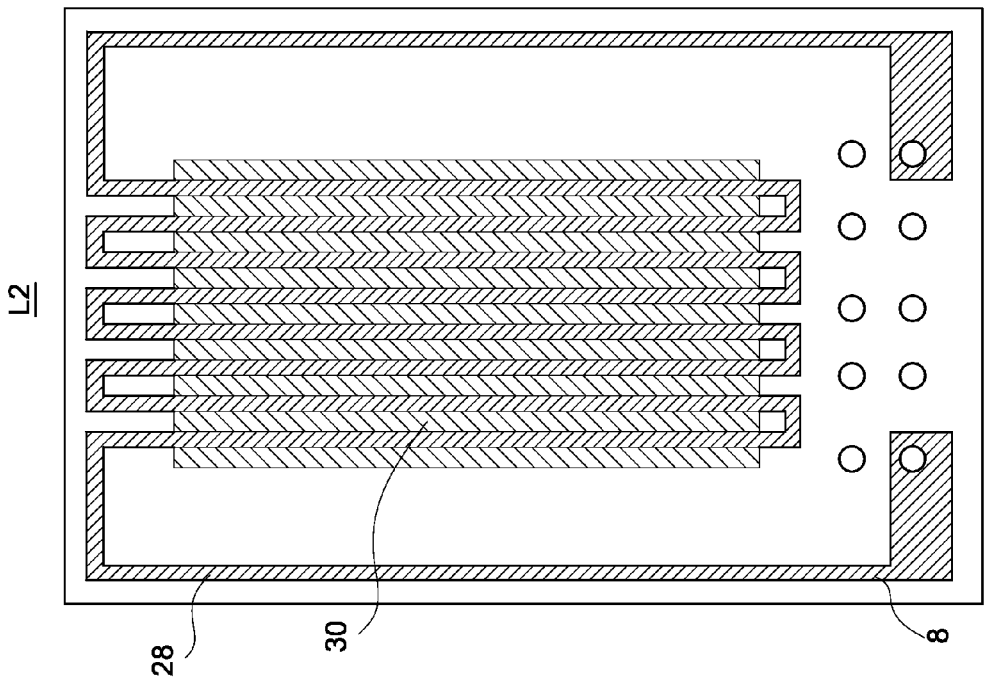
Figure 10B:
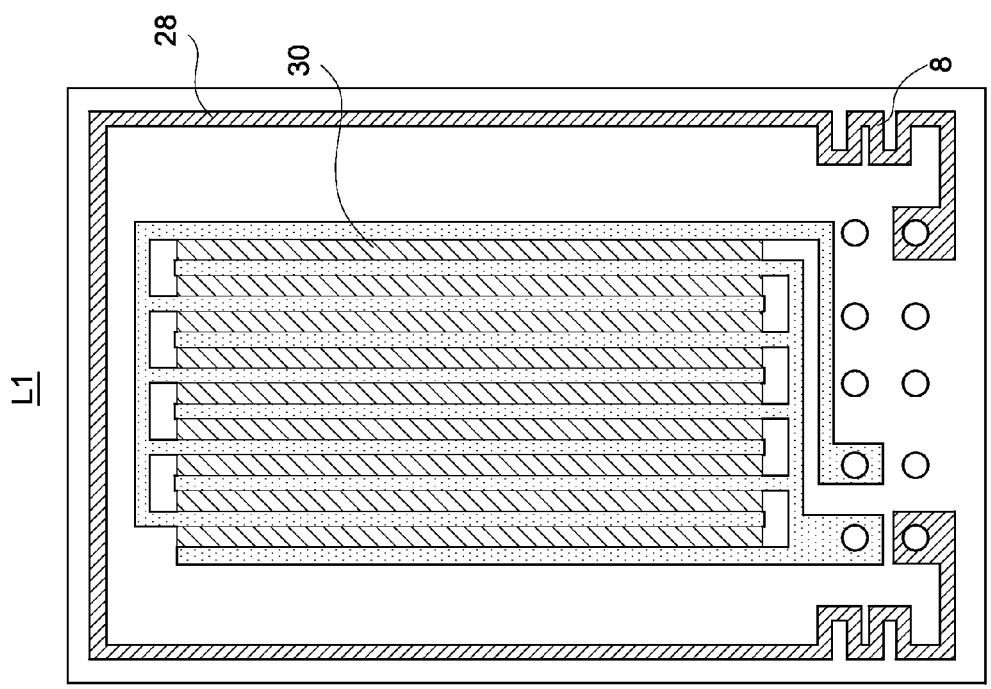

FIGS. 8A to 8D are top view of the PID 1 comprising an integrated circuit board 28 with holes. FIGS. 8A, 8B, 8C, and 8D illustrate four different layers L1, L2, L3 and L4 respectively, wherein the heating elements or heaters are present on all four layers and the heating elements are connected in series through layer interconnects. In L1, L2, L3 and L4, the heating elements also act as fence electrodes. In layer L3, the heating element has a long serpentine design, and the length may be about 1m. FIG. 8D shows the layer L4, which further comprises the temperature feedback control circuit 16. The electrodes in FIG. 8A are straight-line electrodes. Similar designs also exist with slot openings as shown in FIGS. 9A to 9D. Another set of examples of PIDs with various designs of integrated circuit boards are illustrated in FIGS. 10A to 10D. The design of FIGS. 10A to 10D are same as mentioned above, however, the integrated circuit board 28 is longer than the previous one. The length of the integrated circuit board is about 38 mm, and width of about 12 mm.

EXAMPLES

Measurements of the ionization current were performed with a pair of ion sensing electrode as shown in FIG. 5. Ion current was converted to voltage by a transimpedance amplifier. The collected signal was analyzed using Labview software. Human breath tests were conducted to evaluate the functionality of the PID. During the breath sample tests, samples were collected from human through a bacteria filter mouthpiece (Vacumed MQ303) connected directly to the gas line. Water condensation may results from moisture present in breath. To avoid water condensation, the PID sensor chip was heated to about 80° C. by an integrated on-chip heater.

Example 1

In human breath, the gas flow rate or pressure during breathing varies from person to person. Separate tests showed that the variation of breath flow rate in the range of 2~15 L/min is possible. The change of flow rate affects the PID sensor's baseline signal (background signal when acetone is absent), leading to inaccuracy of ion measurement. Tests have indicated that the PID's baseline voltage could change ~70 mv when gas flow rate was varied from 1 to 20 L/min. The cause for the baseline change might partially because the incoming gas directly impacted on the lamp and sensor electrodes, which resulted a number of effects, such as abrupt changes of temperature, flow rate, relative position, and humidity in the ionization zone, one or the combination of which might result in change of sensor baseline voltage. To mitigate this issue, a gas diffuser plate was designed and implemented in the gas chamber immediately before the PID sensor. The "I" shaped diffuser splits the incoming gas into two side-streams and blocks direct impact of the gas flow on the sensor electrodes. Tests showed this method was able to reduce baseline voltage variation to about 6 mV in 1 to 20 L/min flow rate range.

Figure 11:
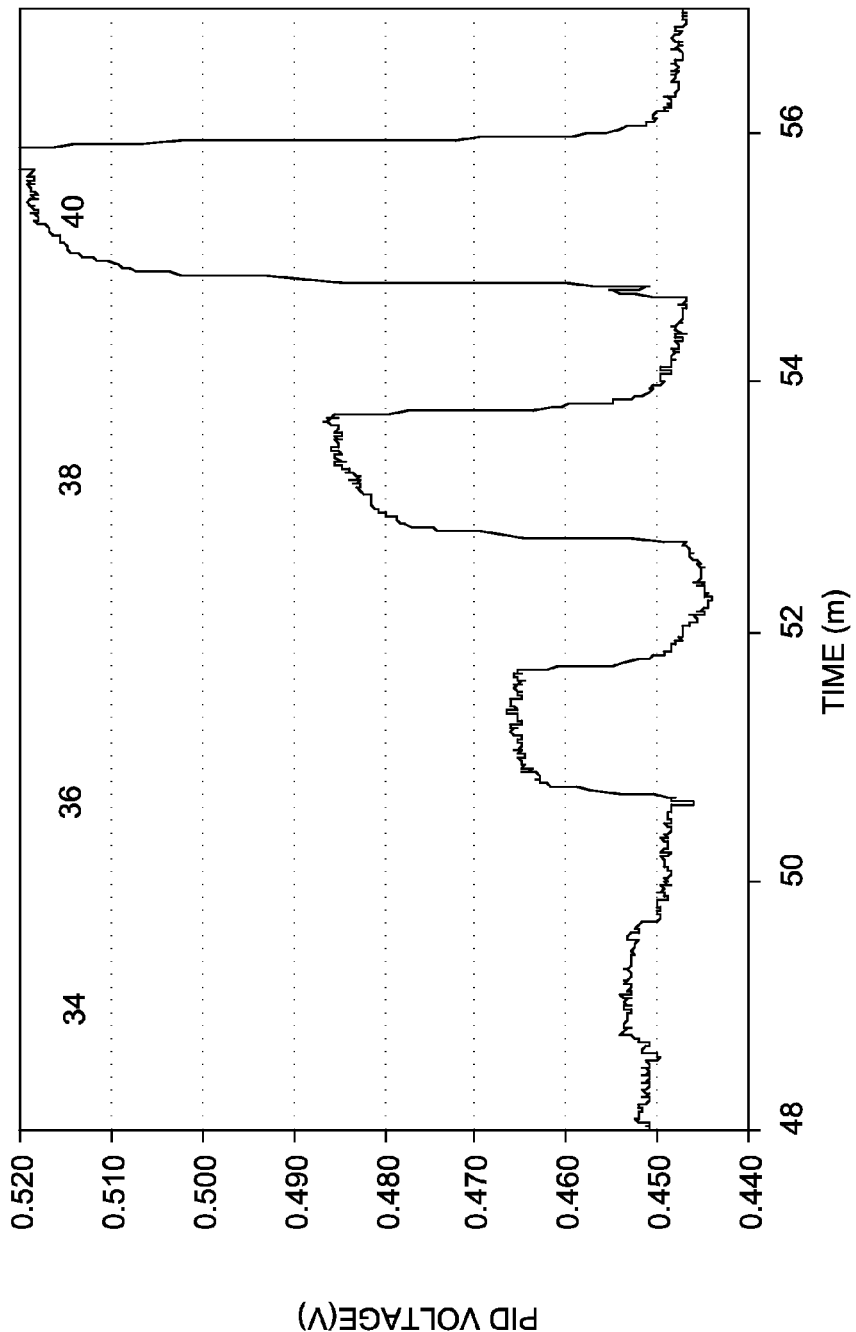
FIG. 11 is a calibration graph of a PID of the invention.

For calibration, the PID sensor was subjected to dry acetone-nitrogen gas mixtures with different acetone concentrations. FIG. 11 shows the calibration data of a PID sensor, and the signal peaks illustrate the output voltage of the sensor at different acetone concentrations, where a 10 eV UV lamp was used. 34, 36, 38 and 40 are the signal peaks for 0.1 ppm, 0.5 ppm, 1 ppm, and 2 ppm acetone concentration respectively.

Example 2

Figure 12:
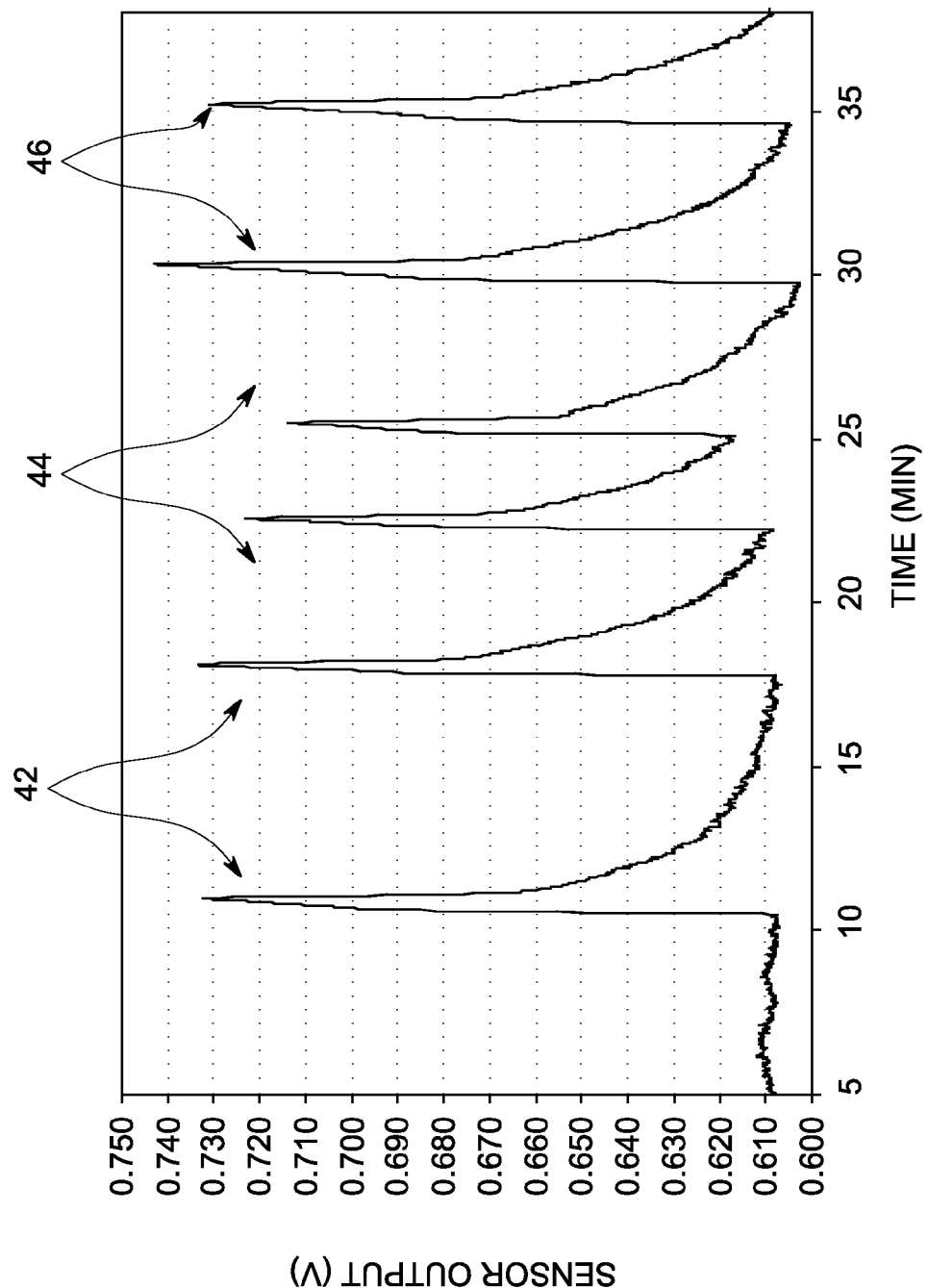
FIG. 12 is a graph of a signal output of a PID of the invention to measure various components of breath sample collected from three different subjects before food intake.

In fat-metabolism, the decarboxylation of acetoacetate generates acetone, which is one of the most abundant endogenous compounds in human breath. An amount of acetone in healthy subjects is in a range of about 0.2-10 ppm, and acetone is higher in patients having uncontrolled diabetes. The tests were performed by collecting samples from three different human individuals at two different times of a day. Two breath samples were collected from each human individual through a mouthpiece containing a bacteria filter (Vacuumed MQ303) connected directly to the gas line. The PID sensor was pre-heated to 79° C. to prevent water condensation from human breath. One sample was collected about 1 hour before lunch and another sample was collected about 1 hour after lunch. FIG. 12 and Table 1 show the sensor response pattern (output voltage) for the breath acetone as detected by the PID. Comparing the signals obtained before (FIG. 12) and after (data not shown) lunch, as shown in Table 1, the breath acetone concentration was dropped about 20% after lunch, wherein the sensor output in Volts (in the plot of FIG. 12) represents amount of acetone present in the breath sample in ppm. This result is consistent with the general understanding of the reduced fat metabolism after meal, wherein the amount of acetone is within a typical breath acetone range. The delayed drop (tail) of each signal peak may be due to the slow exiting residual gas in the gas line, which is about 5 feet (4 mm I.D., ~19 mL in volume) in the bench top setup for this test. As a result, the PID was able to quantify an amount of various compounds present in different gas mixture of the breath sample.

TABLE 1

| Subject | Before lunch (mV) | | | After lunch (mV) | | | Change (mV) | Change (%) |
| --- | --- | --- | --- | --- | --- | --- | --- | --- |
| | Sample 1 | Sample 2 | Average | Sample 1 | Sample 2 | Average | | |
| 1 | 126 | 123 | 124.5 | 98 | 94 | 96 | −28.5 | −22.9% |
| 2 | 114 | 103 | 108.5 | 96 | 76 | 86 | −22.5 | −20.7% |
| 3 | 138 | 126 | 132 | 112 | 100 | 106 | −26 | −19.7% |

In comparison, two commercially available PID sensors (for example, sensor 1 & 2), which were used as control, showed different levels of malfunction for human breath test (data not shown). The response pattern (or signal) of sensor 1 was unable to return to the baseline with time and the data was inconsistent between two different samples collected consecutively from the same human individual. Sensor 2 showed slight drops from baseline when breath samples were provided, instead of positive signal peaks (data not shown). Since sensors 1 and 2 functioned well in prior dry gas tests, the malfunction of the sensors for human breath sample is assumed due to the high humidity of human breath, which could condense and form conductive path between the sensor electrodes at room temperature. Therefore, the disclosed PID was able to quantify amount of various gases within acceptable margins of error.

Example 3

Various breath-sampling approaches suitable for the PID were tested. In the experiment, three sampling methods were tested, such as, direct blow through a bacteria filter mouthpiece (Vacumed MQ303), pre-sampled breath stored in a 5 L sampling bag (SKC), and pre-sampled breath stored in a 0.25 L GaSampler bag (Quintron).

The 5 L sampling bag showed most consistent results compared to other two sampling approaches. Because of large volume, the 5 L bag supplied a stable gas flow over a period of time to the PID to establish a steady signal output. In the direct blow and an approach with 0.25 L bag, the sensor signal was seen dropping upon stopping of gas flow (stop blowing or empty bag). It is expected that when using a bag to collect breath sample, water vapor tend to condensate on the bag wall, which reduces the water concentration entering into the PID sensor chamber, therefore, reducing the water ion interference. This could explain the smaller signal amplitude with 5 L and 0.25 L bag sample. 0.25 L sample has smallest signal amplitude. This is mainly due to the dead volume of the test setup. It is also noticeable that the breath test signal and baseline is smaller than test data. This is because a lower UV lamp driving voltage is used (4 V down shift to 3.5 V) to extend the lifetime of the UV lamp. A lower driving voltage reduced the UV intensity emitted from the lamp, which changed the PID sensor sensitivity from 40 mV/ppm to 10 mv/ppm.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A photo-ionization detector (PID), comprising:
a substrate comprising
 a gas ionization chamber,
 at least one pair of ion sensing electrodes,
 at least one amplifying circuit to amplify a response signal generated by the ion sensing electrodes to form amplified signals;
 and a heating element;
an ultraviolet (UV) ionization source to transmit a UV light beam into the gas ionization chamber,
wherein the substrate is a multilayered substrate comprising an alternating arrangement of at least four conducting layers insulated by at least three dielectric layers positioned therebetween, the four conducting layers having at least a first layer and at least a third layer each comprising pairs of ion sensing electrodes; at least a second layer comprising a fence electrode to prevent leakage of current between ion sensing electrodes; and at least the fourth layer comprising the heating element;

wherein each of the conducting layers and the dielectric layers are interconnected by multiple open holes or open slots, and the open holes and the open slots provide channels to form the gas ionization chamber throughout said multilayered substrate, and wherein the photo-ionization detector is configured to detect aliphatic hydrocarbons, aromatic hydrocarbons, aldehydes, ketones, or alcohols.

2. The photo-ionization detector of claim 1 further comprises a temperature sensor, and a temperature feedback control circuit in operative association with the substrate.

3. The photo-ionization detector of claim 1 is configured to detect acetone, isoprene, ammonia, or benzene.

4. The photo-ionization detector of claim 1 is configured to detect acetone.

5. The photo-ionization detector of claim 1, wherein the ultraviolet (UV) ionization source is directly fixed on the lamp driver board.

6. The photo-ionization detector of claim 1, wherein the ultraviolet (UV) ionization source transmits ultraviolet (UV) light in a frequency range from about 100 nm to 210 nm.

7. A system comprising the photo-ionization detector of claim 1.

\* \* \* \* \*